(12) United States Patent
Sakhrani et al.

(10) Patent No.: US 7,674,504 B2
(45) Date of Patent: Mar. 9, 2010

(54) ARTICLE WITH LUBRICATED SURFACE AND METHOD

(76) Inventors: Vinay G. Sakhrani, 5505 Rush Springs Ct., Raleigh, NC (US) 27617; Joel L. Williams, 1306 Walnut St., Cary, NC (US) 27511; Charles Tomasino, 4316 Oak Park Rd., Raleigh, NC (US) 27612; Paul M. Vernon, Jr., 310 Brandywine Rd., Chapel Hill, NC (US) 27516

( * ) Notice: Subject to any disclaimer, the term of this patent is extended or adjusted under 35 U.S.C. 154(b) by 0 days.

(21) Appl. No.: 12/018,729

(22) Filed: Jan. 23, 2008

(65) Prior Publication Data

US 2008/0145565 A1 Jun. 19, 2008

Related U.S. Application Data

(62) Division of application No. 10/791,542, filed on Mar. 2, 2004, now Pat. No. 7,431,989.

(60) Provisional application No. 60/468,156, filed on May 6, 2003.

(51) Int. Cl.
*H05H 1/00* (2006.01)
(52) U.S. Cl. ........................ 427/535; 427/457; 427/532; 427/533; 427/536
(58) Field of Classification Search ........................ None
See application file for complete search history.

(56) References Cited

U.S. PATENT DOCUMENTS

| 4,536,179 | A |   | 8/1985  | Anderson et al. |
| 4,767,414 | A |   | 8/1988  | Williams et al. |
| 4,822,632 | A |   | 4/1989  | Williams et al. |
| 4,842,889 | A |   | 6/1989  | Hu et al. |
| 4,844,986 | A |   | 7/1989  | Karakelle et al. |
| 4,876,113 | A |   | 10/1989 | Yasunaga et al. |
| 4,960,609 | A |   | 10/1990 | Homola et al. |
| 5,225,659 | A | * | 7/1993  | Kusano et al. ......... 219/121.59 |
| 5,331,487 | A |   | 7/1994  | Gregory et al. |

(Continued)

FOREIGN PATENT DOCUMENTS

JP          06-304243          11/1994

OTHER PUBLICATIONS

Popov, O.A. (1995). "High Density Plasma Sources—Design, Physics and Performance." William Andrew Publishing/Noyes. pp. 1-4 and 30-33.*

(Continued)

*Primary Examiner*—Michael Cleveland
*Assistant Examiner*—Joel G Horning
(74) *Attorney, Agent, or Firm*—The Law Office of David P. Hendricks, PLLC

(57) ABSTRACT

A method for preparing one or more lubricated surfaces of an article to reduce the break-out force and sliding frictional force. A lubricant is applied to one or more surfaces, and the lubricant-coated surface is treated by exposing the surface to an energy source, wherein the energy source is an ionizing gas plasma at about atmospheric pressure, gamma radiation, or electron beam radiation. One or more of the surfaces may be exposed to the ionizing gas plasma at about atmospheric pressure prior to application of the lubricant. Another aspect of the invention is articles produced using one or more methods of the invention.

20 Claims, 14 Drawing Sheets

U.S. PATENT DOCUMENTS

| | | | |
|---|---|---|---|
| 5,338,312 A | | 8/1994 | Montgomery |
| 5,409,738 A | * | 4/1995 | Matsunuma et al. ........ 427/502 |
| 5,591,481 A | | 1/1997 | Takahashi et al. |
| 5,830,577 A | * | 11/1998 | Murayama et al. ....... 428/411.1 |
| 5,895,558 A | * | 4/1999 | Spence ....................... 204/164 |
| 6,090,081 A | * | 7/2000 | Sudo et al. .................. 604/230 |
| 6,221,434 B1 | | 4/2001 | Visca et al. |

OTHER PUBLICATIONS

S. Crystal Coley et al., "Performance of three portable infusion-pump devices set to deliver 2 ml/hr", Am. Jrnl. of Health-System Pharmacists, vol. 54, Jun. 1, 1997, pp. 1277-1280.

Jody L. Carl et al., "Fluid delivery from infusion-pump syringes", Am. Jrnl. of Health-System Pharmacists, vol. 52, Jul. 1, 1995, pp. 1428-1432.

T. Neff, et al., "Evaluation of the Faststart mode for reducing start-up delay in syringe pump infusion systems", Swiss Medical Weekly, vol. 131, 2001, pp. 219-222.

R. Ferrari and D.R. Beech, "Infusion Pumps: guidelines and pitfalls", Australian Provider, vol. 18, No. 2, 1995.

A. Leibmann-Vinson, et al., "Physics of Friction in Disposable Plastic Syringes", The American Physics Society meeting, Mar. 1997, Session J32.02.

* cited by examiner

ARTICLE WITH LUBRICATED SURFACE AND METHOD

CROSS-REFERENCE TO RELATED APPLICATIONS

The present application is a divisional application that claims priority from U.S. patent application Ser. No. 10/791,542 filed on Mar. 2, 2004, entitled "Article with Lubricated Surface and Method," which has subsequently issued as U.S. Pat. No. 7,431,989, which in turn claims the benefit of Provisional Application No. 60/468,156 filed May 6, 2003, entitled "Article Having Single-Layered Lubricant and Method Thereof."

BACKGROUND

It is well known in the art that friction is the resistant force that prevents two objects from sliding freely when in contact with one another. There are a number of different types of frictional forces depending upon the particular motion being observed. Static friction is the force that holds back a stationary object up to the point where the object begins to move. Kinetic friction is the resistive force between two objects in motion that are in contact with one another. For any two objects in contact with one another, a value known as the coefficient of friction can be determined which is a relative measure of these frictional forces. Thus, there is a static coefficient of friction and a kinetic coefficient of friction. Stated another way, the coefficient of friction relates to the amount of force necessary to initiate movement between two surfaces in contact with one another, or to maintain this sliding movement once initiated. Because of their chemical composition, physical properties, and surface roughness, various objects have different coefficients of friction. Softer, more compliant materials such as rubber and elastomers tend to have higher coefficient of friction values (more resistance to sliding) than less compliant materials. The lower the coefficient of friction value, the lower the resistive force or the slicker the surfaces. For example, a block of ice on a polished steel surface would have a low coefficient of friction, while a brick on a wood surface would have a much higher coefficient of friction.

The difference between the static and kinetic coefficients of friction is known as "stick-slip." The stick-slip value is very important for systems that undergo back-and-forth, stop-and-go, or very slow movement. In such systems, a force is typically applied to one of the two objects that are in contact. This force must be gradually increased until the object begins to move. At the point of initial motion, referred to as "break-out," the static friction has been overcome and kinetic frictional forces become dominant. If the static coefficient of friction is much larger than the kinetic coefficient of friction, then there can be a sudden and rapid movement of the object. This rapid movement may be undesirable. Additionally, for slow moving systems, the objects may stick again after the initial movement, followed by another sudden break-out. This repetitive cycle of sticking and break-out is referred to as "stiction."

In order to minimize the friction between two surfaces, a lubricant can be applied which reduces the force required to initiate and maintain sliding movement. However, when two lubricated surfaces remain in contact for prolonged periods of time, the lubricant has a tendency to migrate out from the area of contact due to the squeezing force between the two surfaces. This effect tends to increase as the squeezing force increases. As more of the lubricant migrates from between the two surfaces, the force required to initiate movement between the surfaces can revert to that of the non-lubricated surfaces, and stiction can occur. This phenomenon can also occur in slow moving systems. Because of the slow speed, the time interval is sufficient to cause the lubricant to migrate away from the area of contact. Once the object moves past the lubricant-depleted area, the object comes into contact with a lubricant-rich area. The frictional force is less in the lubricant-rich area and sudden, rapid movement of the object can occur.

Attempts have been made to reduce the migration of lubricant from between surfaces in contact with one another. In particular, methods exist using an energy source to treat a lubricant applied to one or more of the surfaces such that the migration is reduced.

Information relevant to attempts to address the above problems using a gas plasma as the energy source for several specific embodiments can be found in the following U.S. patents: U.S. Pat. No. 4,536,179; No. 4,767,414; No. 4,822,632; No. 4,842,889; No. 4,844,986; No. 4,876,113; No. 4,960,609; No. 5,338,312; and No. 5,591,481. However, each one of these references suffers from the disadvantage of treating the lubricant layer with an ionizing gas plasma generated under vacuum, rendering the methods impractical for large-scale production operations.

A need exists, therefore, for a method to produce a lubricated surface in which the migration of lubricant from the area of contact between two surfaces is reduced such that the break-out force and sliding frictional force are minimized, such method not being conducted under vacuum. A need also exists for articles produced by such a method.

SUMMARY

The present invention is directed to a method and articles that satisfy these needs. One aspect of the invention comprises a method to reduce the migration of lubricant between surfaces in sliding frictional contact with one another. A lubricant is applied to one or more of the surfaces, then the lubricant is exposed to an energy source at about atmospheric pressure to treat the lubricant. Another aspect of the invention comprises using an ionizing gas plasma at about atmospheric pressure as the energy source. Yet another aspect of the invention comprises using ionizing radiation as the energy source, such as gamma radiation produced by, for example, cobalt-60 and cesium-137 sources. Still another aspect of the invention comprises using electron beam radiation as the energy source. Yet another aspect of the invention comprises additionally exposing the surface to the ionizing gas plasma prior to application of the lubricant. The reduced migration of the lubricant minimizes the stiction phenomenon common to surfaces in sliding contact with one another, thereby reducing the break-out force and sliding frictional force.

Still another aspect of the invention comprises articles produced in accordance with at least one of the methods of the invention to reduce the migration of lubricant from two or more surfaces in contact with one another to minimize stiction. Yet another aspect of the invention comprises articles produced in accordance with one or more of the methods of the invention to minimize the sliding frictional force of a surface of the article.

Definitions

In the description that follows, a number of terms are used. In order to provide a clear and consistent understanding of the specification and appended claims, including the scope to be given such terms, the following definitions are provided:

About Atmospheric Pressure. An embodiment of the invention involves the generation of an ionizing gas plasma. While gas plasmas can be produced under various levels of vacuum, the invention uses a plasma generated at essentially atmospheric pressure. While no conditions of vacuum or above-atmospheric pressure are deliberately produced by carrying out the method of the invention, the characteristics of the gas flow may create a deviation from atmospheric pressure. For example, when using a method of the invention to treat the inside of a cylindrical object, the gas flowing into the cylinder may result in a higher pressure within the cylinder than outside the cylinder.

Break-Out. An embodiment of the invention involves surfaces in sliding contact with one another. When the surfaces are in contact but at rest, a force must be applied to one of the surfaces to initiate movement. This applied force must be increased until the frictional forces opposing movement are overcome. The point at which the applied force just surpasses the frictional force and movement is initiated is known as break-out.

Chatter. Repetitive stick-slip movement associated with the movement of surfaces in contact with one another is known as chatter. When a lubricant is present between the surfaces, chatter can occur when the lubricant is squeezed out from between the surfaces, resulting in an increase in the coefficient of friction. A larger force must then be applied to the surfaces in order to initiate movement, which can cause a sudden, exaggerated movement. Chatter occurs when this cycle is repetitive.

Coefficient of Friction. The coefficient of friction relates to the amount of force necessary to initiate movement between two surfaces in contact with one another, or to maintain this sliding movement once initiated. Numerically, the term is defined as the ratio of the resistive force of friction divided by the normal or perpendicular force pushing the objects together.

Electron Beam Radiation. Electron beam radiation is a form of ionizing radiation produced by first generating electrons by means of an electron gun assembly, accelerating the electrons, and focusing the electrons into a beam. The beam may be either pulsed or continuous.

Friction. Friction is a resistive force that prevents two objects from sliding freely against each other.

Functionalized Perfluoropolyether. A perfluoropolyether where one or more of the fluorine atoms have been replaced by reactive functional groups.

Gamma Radiation. Gamma radiation is a type of electromagnetic waveform, often emitted at the same time the unstable nucleus of certain atoms emits either an alpha or beta particle when the nucleus decays. Gamma radiation, being an electromagnetic waveform, is similar to visible light and x-rays but of a higher energy level which allows it to penetrate deep into materials.

Gas Plasma. When sufficient energy is imparted to a gas, electrons can be stripped from the atoms of the gas, creating ions. Plasma contains free-moving electrons and ions, as well as a spectrum of electrons and photons.

Lubricant-solvent solution (coating solution). The lubricant may be diluted with an appropriate solvent prior to applying the lubricant onto the surface. The resulting mixture of lubricant and solvent is known as a lubricant-solvent solution.

Ionizing. Ionizing means that enough energy is present to break chemical bonds.

Parking. Syringes used in medical applications are often pre-filled prior to use and stored. The amount of time between filling the syringe and discharging the syringe is known as parking time. In general, parking increases the break-out force.

Perfluoropolyether. A perfluoropolyether is a compound with the general chemical structure of:

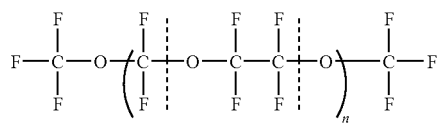

Stiction. The overall phenomenon of stick-slip is known as stiction.

Stick-Slip. The difference between static and kinetic coefficients of friction is known as stick-slip. In systems where a lubricant is present, high mating forces can squeeze the lubricant out from between the surfaces in contact with one another. An increased force is then required to initiate sliding movement of the surfaces. This movement may occur suddenly, caused by the surfaces coming into contact with a lubricant-rich area. If the lubricant is again forced out from between the surfaces, they can begin to bind. The sliding motion can stop until the force is increased enough to once again initiate movement. This alternating sticking and slipping is called stick-slip.

BRIEF DESCRIPTION OF THE DRAWINGS

These and other features, aspects, and advantages of the present invention will become better understood with regard to the following description, appended claims, and accompanying drawings where:

DESCRIPTION

Figure 1:
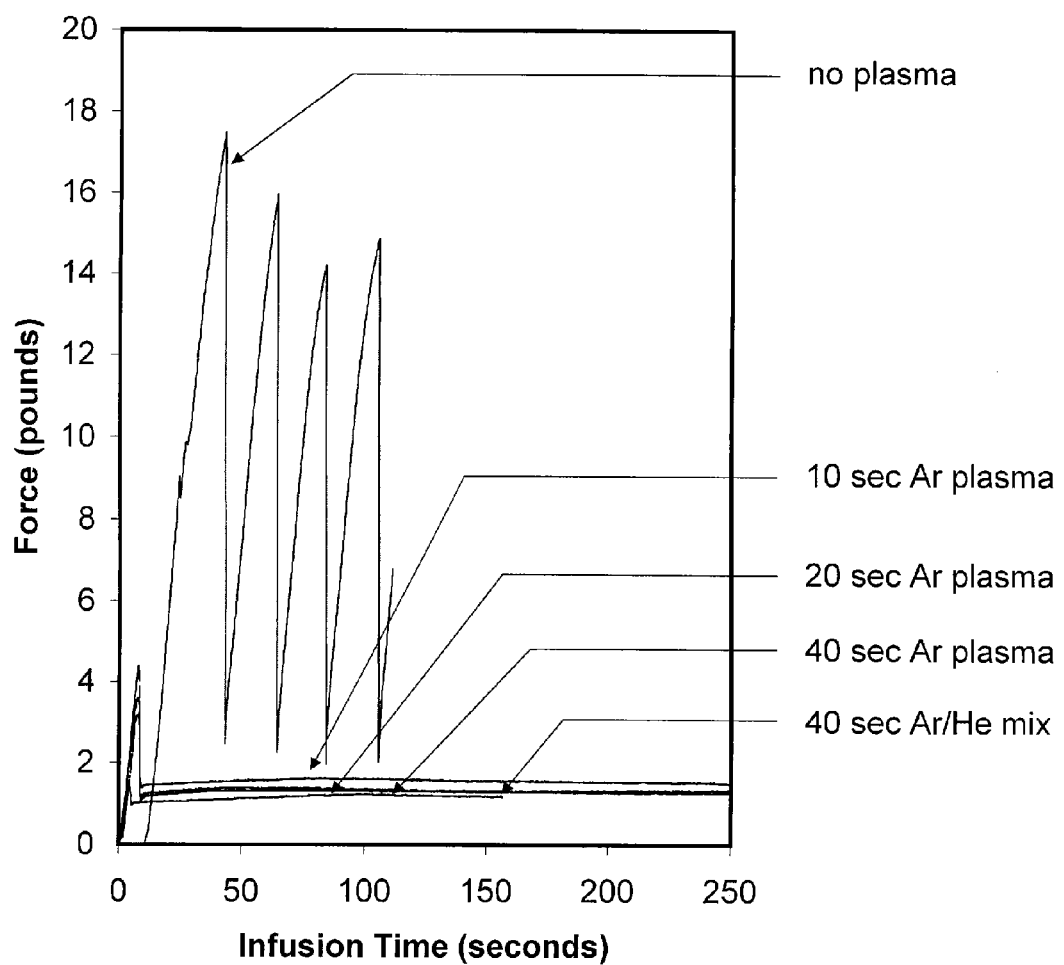
FIG. 1 is a plot of experimental measurements of the force applied to a syringe plunger as a function of infusion time, where the barrel of the syringe was coated with a specific lubricant and treated for various times by an ionizing gas plasma at about atmospheric pressure.

It is understood that the embodiments described herein are intended to serve as illustrative examples of certain embodiments of the present invention. Other arrangements, variations, and modifications of the described embodiments of the invention may be made by those skilled in the art. No unnecessary limitations are to be understood from this disclosure, and any such arrangements, variations, and modifications may be made without departing from the spirit of the invention and scope of the appended claims. Stated ranges include the end points of the range and all intermediate points within the end points.

A method according to the present invention for reducing the migration of lubricant from between surfaces in contact with one another comprises applying a lubricant to one or more of the surfaces, then treating the lubricant-coated surface by exposing it to an energy source. Another method according to the present invention comprises exposing the surface to an energy source, specifically an ionizing gas plasma at about atmospheric pressure, prior to the application of the lubricant. It is theorized that exposing the surface to the ionizing gas plasma at about atmospheric pressure prior to applying the lubricant creates active sites on the surface that facilitate the reduced migration of the lubricant. As a result of these methods, the lubricant resists migrating from between the surfaces in contact with one another, thereby reducing the break-out force and sliding frictional force. Optionally, any of the methods of the present invention can be applied to only one surface of an object.

The lubricant can be applied to the surface of the object by any of the numerous methods know in the art. By way of example, suitable application methods include spraying, atomizing, spin casting, painting, dipping, wiping, tumbling, and ultrasonics. The method used to apply the lubricant is not essential to the performance of the invention.

The lubricant may be a fluorochemical compound or a polysiloxane-based compound. In one embodiment of the present invention, the fluorochemical compound is a perfluoropolyether (PFPE). Representative examples of commercially available PFPE include, for example, Fomblin M® and Fomblin Y® families of lubricants from Solvay Solexis, Krytox® from E.I. du Pont de Nemours and Company, and Demnum™ from Daikin Industries, Limited. Table 1 presents the chemical structures of these compounds, and Table 2 presents the molecular weights and viscosities. In another embodiment of the invention, the lubricant is a functionalized PFPE. Representative examples of commercially available functionalized PFPE include, for example, Fomblin ZDOL®, Fomblin ZDOL TXS®, Fomblin ZDIAC®, Fluorolink A10®, Fluorolink C®, Fluorolink D®, Fluorolink E®, Fluorolink E10®, Fluorolink E10®, Fluorolink L®, Fluorolink L10®, Fluorolink S10®, Fluorolink T®, and Fluorolink T10®, from Solvay Solexis as shown in Table 3. In yet another embodiment of the invention, the functionalized PFPE may be an emulsion. Representative example of commercially available functionalized PFPE emulsions are, for example, Fomblin FE-20C® and Fomblin FE-20AG® from Solvay Solexis. In yet another embodiment of the invention, the fluorochemical compound is a chlorotrifluoroethylene. A representative example of commercially available chlorotrifluoroethylene is, for example, Daifloil™ from Daikin Industries, Limited (see Table 2). In still another embodiment of the invention, the polysiloxane-based compound is a silicone oil with a dimethlypolysiloxane chemical formulation of the following general chemical structure:

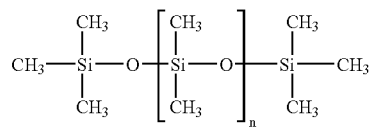

where n = 10-50,000

The number of repeating siloxane units (n) in the polymer chain will determine the molecular weight and viscosity of the silicone oil. As the number of siloxane units increases, the polymer becomes longer and both the molecular weight and viscosity increases. Generally, the usable viscosity range of silicone oils is about 5-100,000 centistokes.

The lubricant can be applied in a diluted or non-diluted form, and combinations of diluted or non-diluted lubricants can be used. The lubricant can also be applied as a water dispersion or as an emulsion. Any suitable solvent can be used as the diluent that is compatible with the lubricant or combination of lubricants used. By way of example, a perfluorinated solvent can be used with a perfluoropolyether lubricant. The resulting mixture of one or more lubricants and one or more solvents is known as a lubricant-solvent solution. The lubricant may be diluted in order to facilitate the application of a thin film of the lubricant onto the surface of the object. The amount of dilution, or weight percent of lubricant in the lubricant-solvent solution, is not essential to the performance of the invention. The weight percent of lubricant in the solvent, when a solvent is used, may be greater than or equal to about 0.1 percent, such as, for example, 1, 10, 20, 30, 40 and 50. The weight percent of the lubricant in the solvent may also be less than or equal to about 95 percent, such as, for example, 90, 80, 70, and 60. The diluent solvent is evaporated prior to exposure to the energy source.

For commercialization purposes when a lubricant-solvent solution is used, it may be advantageous to heat the surface after applying the lubricant-solvent solution but before exposing the coated surface to the energy source. The purpose of this step is to facilitate the evaporation of the solvent. When articles are mass-produced according to the methods of the present invention, it may be necessary to minimize the time between application of the lubricant-solvent mixture and exposing the coated surface to the energy source. Therefore, the heating step will cause the solvent to evaporate quicker than at ambient conditions. While the solvent can be evaporated at ambient conditions, elevated temperatures up to about 150° C. can be used. Depending on the surface material, the heating step generally can be carried out at any convenient temperature between ambient and about 150° C., generally in the range of about 80° C. to about 130° C. The amount of time that the coated surface is heated depends on a number of factors including, by way of example, the viscosity and vapor pressure of the solvent, the thickness of the lubricant-solvent solution layer applied to the surface, and the geometric configuration of the surface. The amount of time the coated surface is heated may be greater than or equal to about 0.5 minute, such as, for example, 1, 5, 10, and 20 minutes. The amount of time the coated surface is heated may also be less than about 60 minutes, such as, for example, about 50, 40, and 30 minutes.

In addition to being diluted prior to application, the lubricant may also include additives. The additives include, for example, free radical initiators such as peroxides and azo nitriles; viscosity modifiers or thickening agents such as fluoroelastomers, silica, and Teflon® particles; surfactants or wetting agents; anticorrosion or rust inhibiting agents, antioxidants, antacids, antiwear agents, buffering agents, and dyes.

In one embodiment of the invention, the energy source is an ionizing gas plasma. The gas may be a noble gas including, for example, helium, neon, argon, and krypton. Alternatively, the gas may be an oxidiative gas including, for example, air, oxygen, carbon dioxide, carbon monoxide, and water vapor. In yet another alternative, the gas may be a non-oxidative gas including, for example, nitrogen and hydrogen. Mixtures of any of these gases may also be used.

The exact parameters under which the ionizing gas plasma are generated are not critical to the methods of the invention. These parameters are selected based on factors including, for example, the gas in which the plasma is to be generated, the electrode geometry, radio frequency of the power source, and the dimensions of the surface to be treated. The treatment time may range from about 0.001 second to about 10 minutes, in addition ranging from about 0.001 second to about 5 minutes, and further in addition ranging from about 0.01 second to about 1 minute. The radio frequency may range from about 0.5 kilohertz to about 15,000 kilohertz, in addition ranging from about 1 kilohertz to about 100 kilohertz, and further in addition ranging from about 3 kilohertz to about 10 kilohertz. The power setting may be less than or equal to, for example, about 1 kilowatt.

In another embodiment of the invention the lubricant-coated surface is exposed to ionizing radiation which provides the energy necessary to treat the lubricant. The ionizing radiation source can be gamma radiation or electron-beam radiation. Typically, commercial gamma irradiation processing systems use cobalt-60 as the gamma radiation source, although cesium-137 or other gamma radiation source may also be used. Commercial electron-beam radiation systems generate electrons from an electricity source using an electron gun assembly, accelerate the electrons, then focus the electrons into a beam. This beam of electrons is then directed at the material to be treated. The lubricant-coated surface may be exposed to an ionizing radiation dosage ranging from about 0.1 megarad to about 20 megarads, in addition ranging from about 0.5 megarad to about 15 megarads, and further in addition ranging from about 1 megarad to about 10 megarads.

TABLE 1

CHEMICAL STRUCTURE OF EXAMPLE PERFLUOROPOLYETHER (PFPE) COMPOUNDS

| PFPE Compound | Chemical Structure |
|---|---|
| Fomblin M ® and Fomblin Z ® (Solvay Solexis) | $CF_3[(-O-CF_2-CF_2)p-(O-CF_2)q]-O-CF_3$ <br> (p + q = 40 to 180 and p/q = 0.5 to 2) |
| Fomblin Y ® (Solvay Solexis) | $CF_3[(-O-CF(CF_3)-CF_2)m-(O-CF_2)n]-O-CF_3$ <br> (m + n = 8 to 45 and m/n = 20 to 1,000) |
| Krytox ® (E.I. du Pont de Nemours and Company) | $F-(CF(CF_3)-CF_2-O)n-CF_2-CF_3$ <br> (n = 10 to 60) |
| Demnum ™ (Daikin Industries, Limited) | $F-(CF_2-CF_2-CF_2-O)n-CF_2-CF_3$ <br> (n = 5 to 200) |

TABLE 2

MOLECULAR WEIGHT AND VISCOSITY OF EXAMPLE
PERFLUOROPOLYETHER (PFPE) COMPOUNDS

| PFPE Compound | Molecular Weight (atomic mass units) | Viscosity (centistokes, 20° C.) |
|---|---|---|
| Fomblin M ® and Fomblin Z ® (Solvay Solexis) | 2,000-20,000 | 10-2,000 |
| Fomblin Y ® (Solvay Solexis) | 1,000-10,000 | 10-2,500 |
| Krytox ® (E.I. du Pont de Nemours and Company) | 500-12,000 | 7-2,000 |
| Demnum ™ (Daikin Industries, Limited) | 1,000-20,000 | 10-2,000 |
| Daifloil ™ (Daikin Industries, Limited) | 500-1,100 | 5-1,500$^a$ |

$^a$Viscosity at 25° C.

TABLE 3

FUNCTIONAL GROUPS, MOLECULAR WEIGHT, AND VISCOSITY OF
FUNCTIONALIZED PERFLUOROPOLYETHER (PFPE) COMPOUNDS

| Functionalized PFPE Compound | Functional Group | Number of Functional Groups per Molecule | Molecular Weight (atomic mass units) | Viscosity (centistokes, 20° C.) |
|---|---|---|---|---|
| Fomblin ZDOL ® Fluorolink D ® (Solvay Solexis) | Alcohol —CH$_2$(OH) | 1-2 | 1,000-4,000 | 50-150 |
| Fomblin ZDOL TXS ® Fluorolink E ® Fluorolink E10 ® (Solvay Solexis) | Alcohol —CH$_2$(OCH$_2$CH$_2$)nOH | 1-2 | 1,000-2,500 | 80-150 |
| Fluorolink T ® Fluorolink T10 ® (Solvay Solexis) | Alcohol —CH$_2$OCH$_2$CH(OH)CH$_2$OH | 2-4 | 1,000-3,000 | 2,000-3,000 |
| Fomblin ZDIAC ® Fluorolink C ® (Solvay Solexis) | Alkly Amide —CONHC$_{18}$H$_{37}$ | 1-2 | 1,800 | Wax |
| Fluorolink L ® Fluorolink L10 ® (Solvay Solexis) | Ester —COOR | 1-2 | 1,000-2,000 | 10-25 |
| Fluorolink S10 ® (Solvay Solexis) | Silane | 1-2 | 1,750-1,950 | 170 |
| Fluorolink F10 ® (Solvay Solexis) | Phosphate | 1-2 | 2,400-3,100 | 18,000 |

EXAMPLE 1

Figure 2:
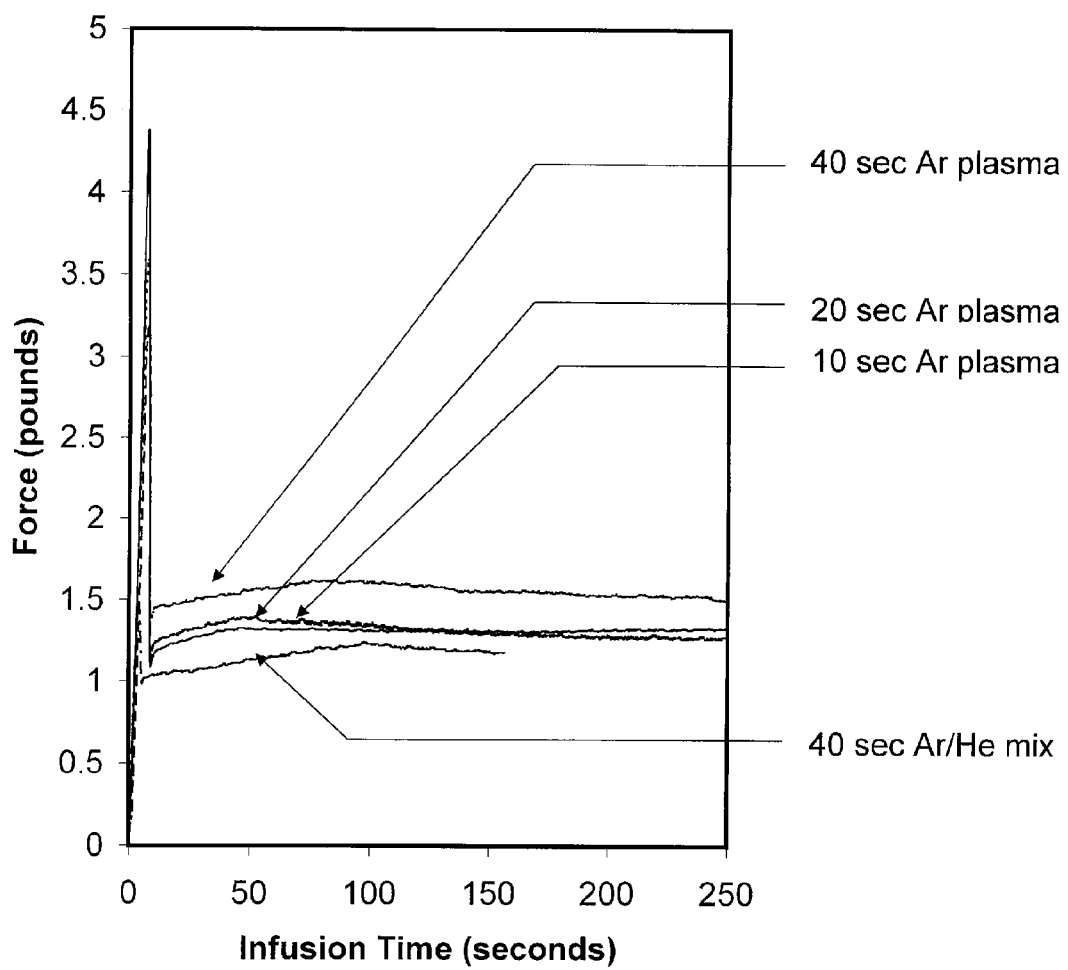
FIG. 2 shows in greater detail a portion of the experimental measurements from FIG. 1.

A coating solution was made by preparing a 90:10 mixture by weight of Fomblin Perfluorosolve™ PFS-1 (Solvay Solexis, Inc.) and Fomblin M100® lubricant. Non-lubricated injection molded 10 cc polypropylene syringe barrels were filled with the coating solution and allowed to drain. The syringe barrels were allowed to air dry to evaporate the solvent, leaving a thin layer of the lubricant on the surface. After drying, the inner cavities of the syringe barrels were exposed to an argon ionizing plasma at about atmospheric pressure for 10, 20, and 40 seconds at an argon gas flow rate of 5 cubic feet per minute (cfm). The syringe barrels were then assembled with non-lubricated plungers and mounted on a motorized syringe pump. The syringe pump was fitted with a digital force gauge to record the compressive forces. The force required to push the plunger down the barrel at an infusion rate of 1 cc/min is shown in FIGS. 1 and 2. FIG. 1 clearly shows that both the break-out force and the stick-slip chatter were dramatically reduced for all of the syringe barrels that were lubricated and plasma treated. The syringe barrel that was lubricated but not plasma treated required a force of about 14 to 18 pounds to achieve break-out and exhibited repeated chatter. All of the syringe barrels that were lubricated and plasma treated required a force of about 3 to 4.5 pounds to achieve break-out and exhibited no discernable chatter. FIG. 2 is an expanded plot showing the effect of the different plasma exposure times.

EXAMPLE 2

Example 1 was repeated except the Fomblin M100® lubricated syringe barrel was exposed to a plasma at about atmospheric pressure using a 50/50 mixture of argon and helium. The gas flow rate was 2.5 cfm argon and 2.5 cfm helium, and the exposure time was 40 seconds. The effect of this argon/helium mixture is also presented in FIGS. 1 and 2.

EXAMPLE 3

Figure 3:
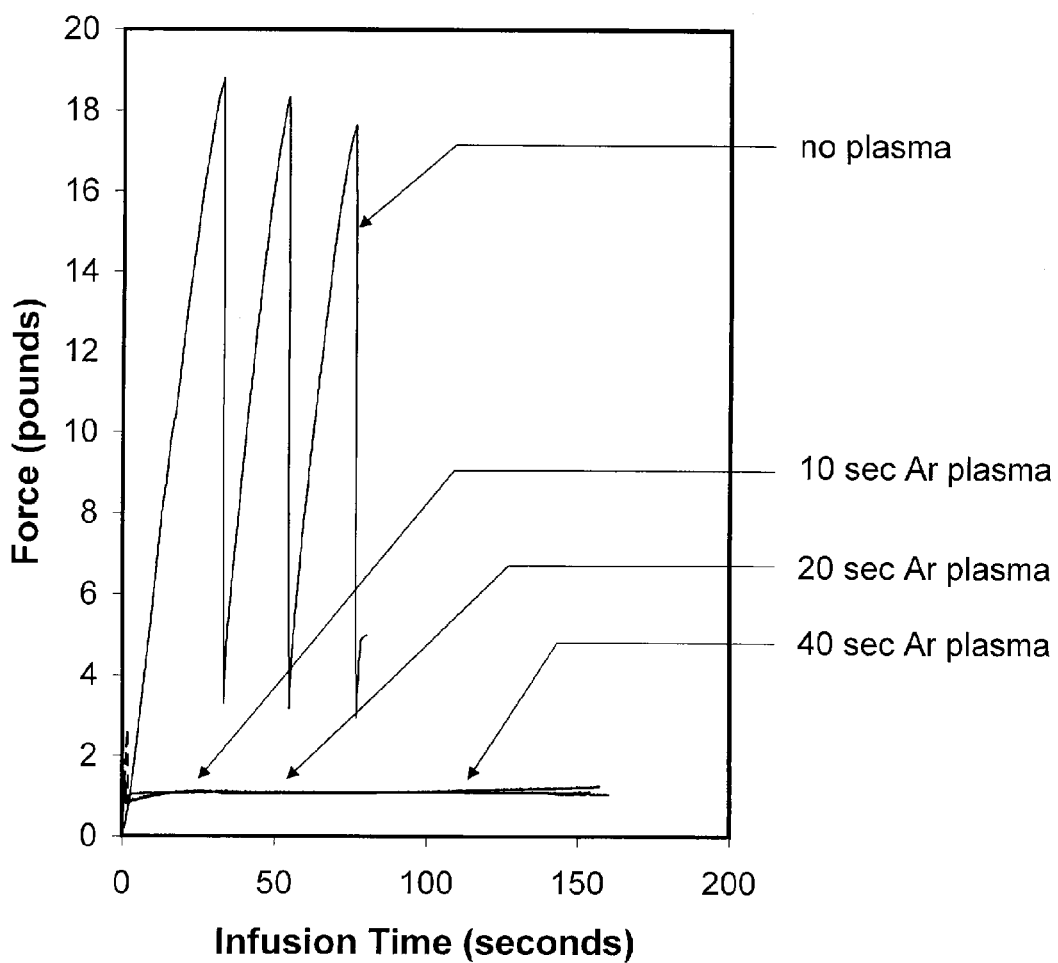
FIG. 3 is a plot of experimental measurements of the force applied to a syringe plunger as a function of infusion time, where the barrel of the syringe was coated with a specific lubricant and treated for various times by an ionizing gas plasma at about atmospheric pressure.

A coating solution was made by preparing a 90:10 mixture by weight of Fomblin Perfluorosolve™ PFS-1 and Fomblin M30® lubricant. Non-lubricated injection molded 10 cc polypropylene syringe barrels were filled with the coating solution and allowed to drain. The syringe barrels were allowed to air dry to evaporate the solvent, leaving a thin layer of lubricant on the surface. After drying, the inner cavity of the syringe barrels were exposed to an argon ionizing plasma at about atmospheric pressure for 10, 20, and 40 seconds at an argon gas flow rate of 5 cfm. The syringe barrels were assembled with non-lubricated plungers and mounted on a motorized syringe pump. The syringe pump was fitted with a digital force gauge to record the compressive forces. The force required to push the plunger down the barrel at an infusion rate of 3 cc/min is shown in FIG. 3. FIG. 3 clearly shows that both the break-out force and the stick-slip chatter were dramatically reduced for all of the syringe barrels that were lubricated and plasma treated. The syringe barrel that was lubricated but not plasma treated required a force of about 17 to 19 pounds to achieve break-out and exhibited repeated chatter. All of the syringe barrels that were lubricated and plasma treated required a force of about 3 pounds to achieve break-out and exhibited no discernible chatter.

EXAMPLE 4

Figure 4:
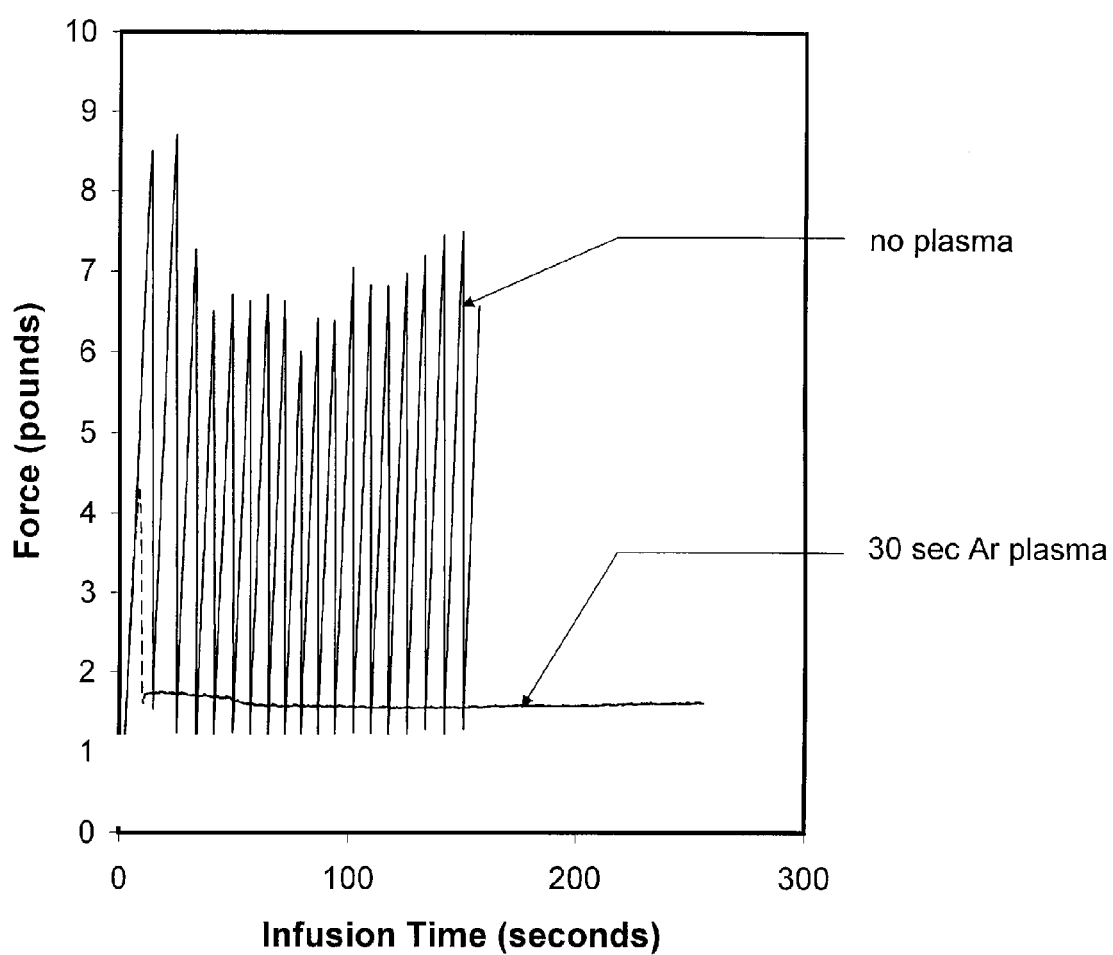
FIG. 4 is a plot of experimental measurements of the force applied to a syringe plunger as a function of infusion time, where the barrel of the syringe was coated with a specific lubricant and treated for 30 seconds by an ionizing gas plasma at about atmospheric pressure.

A coating solution was made by preparing a 95:5 mixture by weight of Fomblin Perfluorosolve™ PFS-1 and Fomblin YR® lubricant. Non-lubricated injection molded 10 cc polypropylene syringe barrels were filled with the coating solution and allowed to drain. The syringe barrels were allowed to air dry to evaporate the solvent, leaving a thin layer of the lubricant on the surface. After drying, the inner cavities of the syringe barrels were exposed to an argon ionizing plasma at about atmospheric pressure for 30 seconds at an argon gas flow rate of 5 cfm. The syringe barrels were assembled with non-lubricated plungers and mounted on a motorized syringe pump. The syringe pump was fitted with a digital force gauge to record the compressive forces. The force required to push the plunger down the barrel at an infusion rate of 1 cc/min is shown in FIG. 4. This figure clearly shows that both the break-out force and the stick-slip chatter were dramatically reduced for all of the syringe barrels that were lubricated and plasma treated. The syringe barrel that was lubricated but not plasma treated required a force of about 6 to 9 pounds to achieve break-out and exhibited repeated chatter. The syringe barrel that was lubricated and plasma treated required a force of about 4 pounds to achieve break-out and exhibited no discernible chatter.

EXAMPLE 5

Figure 5:
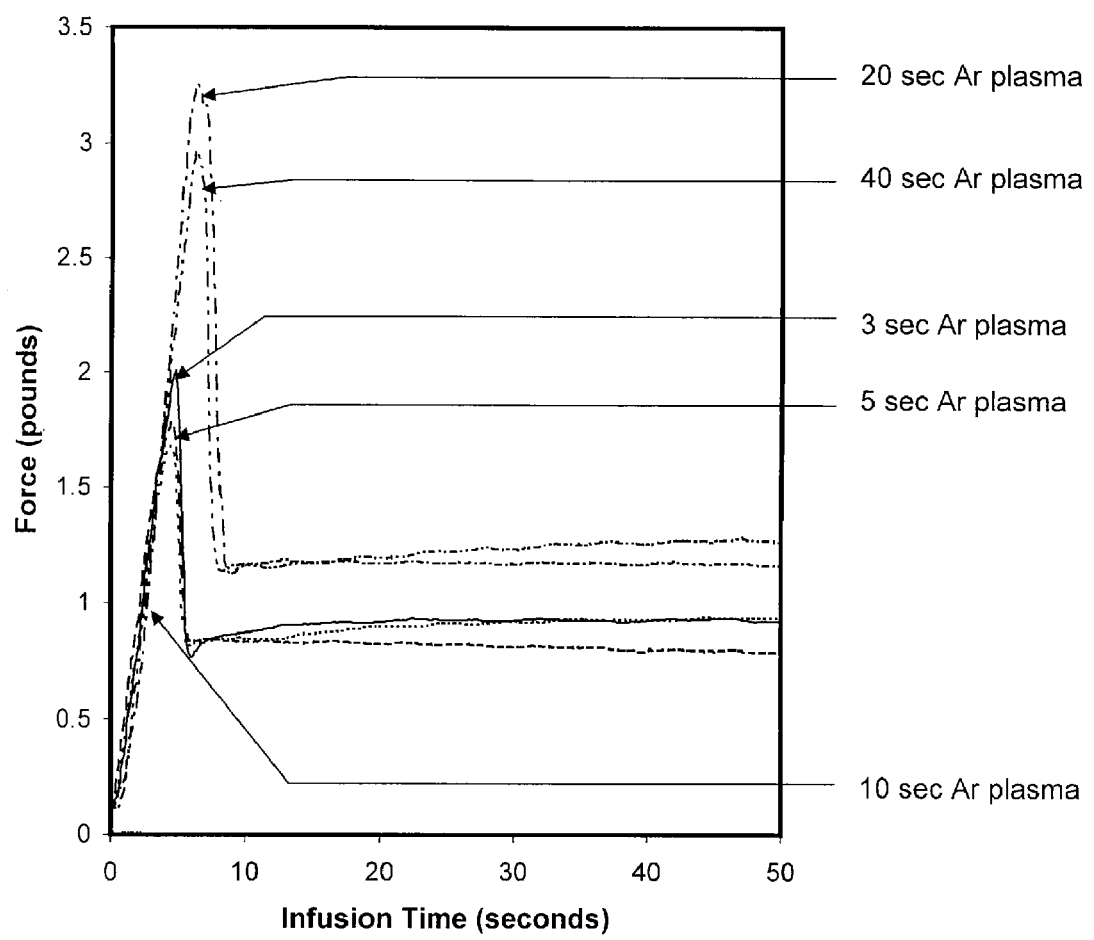
FIG. 5 is a plot of experimental measurements of the force applied to a syringe plunger as a function of infusion time, where the barrel of the syringe was coated with a specific lubricant and treated for various times by an ionizing gas plasma at about atmospheric pressure, then parked for one week.
Figure 6:
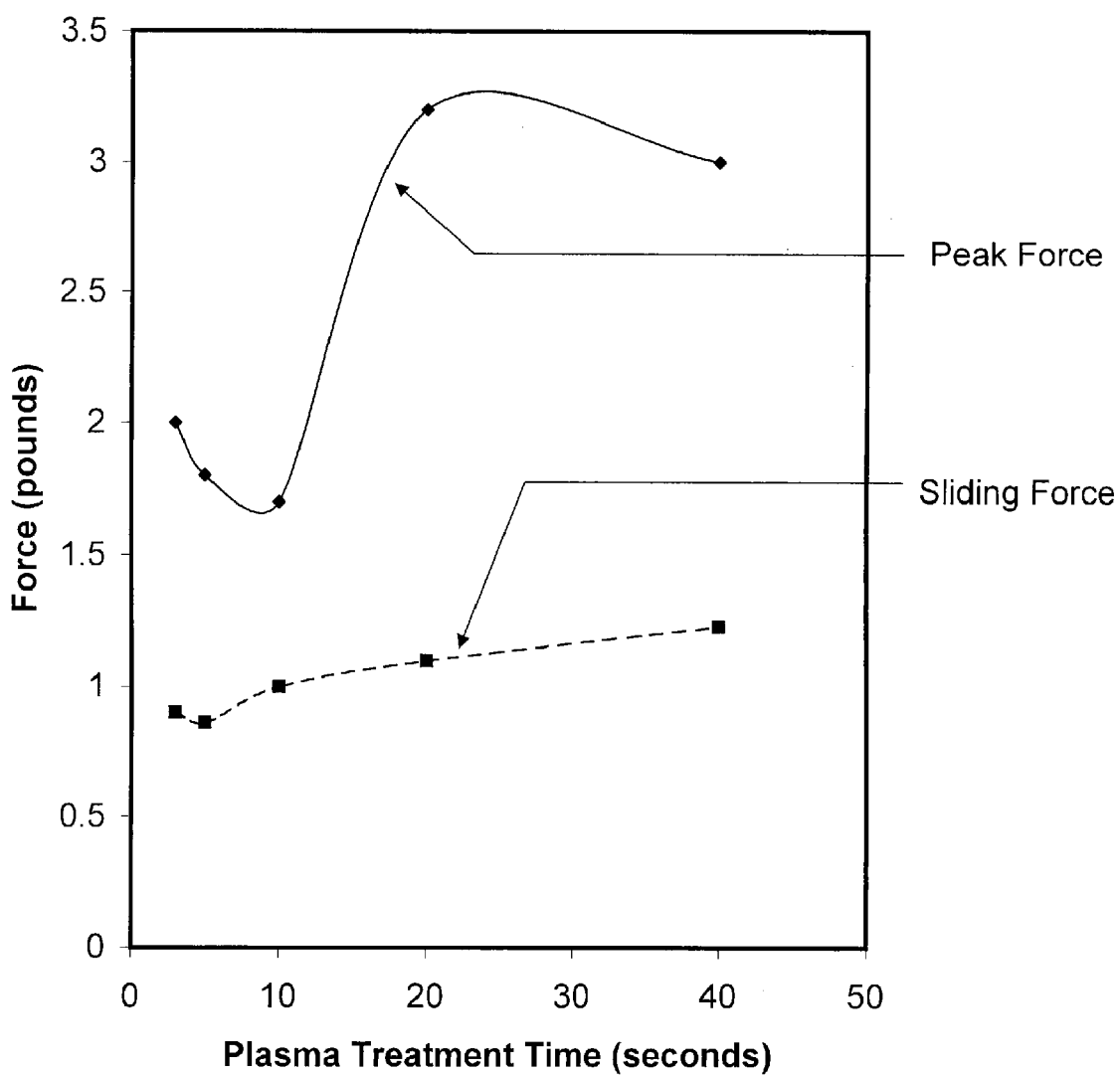
FIG. 6 is a plot of experimental measurements of the break-out force and sliding force applied to a syringe plunger as a function of treatment time with an ionizing gas plasma at about atmospheric pressure.

Example 1 was repeated with plasma exposure times of 3, 5, 10, 20, and 40 seconds. The syringe barrels were lubricated, plasma treated, assembled with plungers, and stored at room temperature for 7 days with the plungers parked in the barrels in the same position for the entire duration before they were tested. The 7-day parking time allowed the applied lubricant coating to achieve equilibrium with respect to any migration on the surface due to compressive forces between the plunger and the barrel. FIG. 5 shows that the break-out force was about 1.5 to 3 pounds and that there was no discernible stick-slip chatter. These results are consistent with the previous examples where there was essentially no parking time between plasma treatment and testing. The data strongly indicate that the lubricant was immobilized by the plasma treatment and did not migrate out from the plunger-barrel interface, even after extended parking times. FIG. 6 plots the break-out force and sliding force versus the plasma treatment time. The data show that the break-out force was influenced by the exposure time to the ionizing plasma, reaching a minimum of about 1.5 pounds at 10 seconds treatment time and then rising to about 3 pounds with increasing treatment time. The sliding force also showed a slight trend of increasing force with increasing treatment time, although generally remaining at about 1 pound.

EXAMPLE 6

Figure 7:
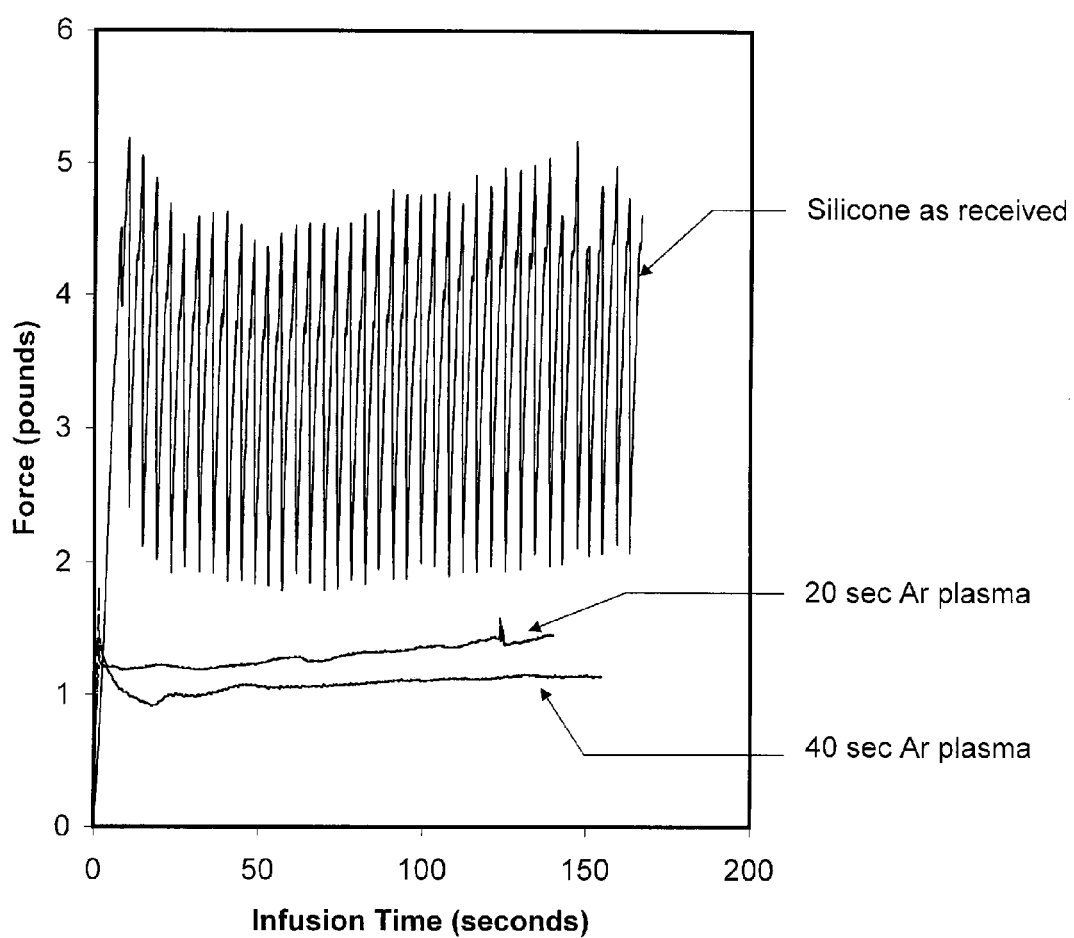
FIG. 7 is a plot of experimental measurements of the force applied to a syringe plunger as a function of infusion time, where the barrel of the syringe was coated with a specific lubricant and treated for various times by an ionizing gas plasma at about atmospheric pressure.

Commercially available syringe barrels pre-lubricated with silicone oil were exposed to an argon ionizing plasma at about atmospheric pressure as described in Example 1. The argon gas flow rate was 5 cfm and the exposure times were 20 and 40 seconds. These syringe barrels were tested identically as described in the previous examples at an infusion rate of 3 cc/min. The resulting data are shown in FIG. 7. These data clearly show that stick-slip chatter is inherent in some commercially available syringes pre-lubricated with silicone oil and that ionizing plasma treatment at about atmospheric pressure dramatically reduced break-out forces and eliminated stick-slip chatter. The syringe barrel that was pre-lubricated but not plasma treated required a force of about 4.5 pounds to achieve break-out and exhibited repeated chatter. The syringe barrels that were pre-lubricated and plasma treated required a force of about 1.5 to 2 pounds to achieve break-out and exhibited no discernible chatter.

EXAMPLE 7

Figure 8:
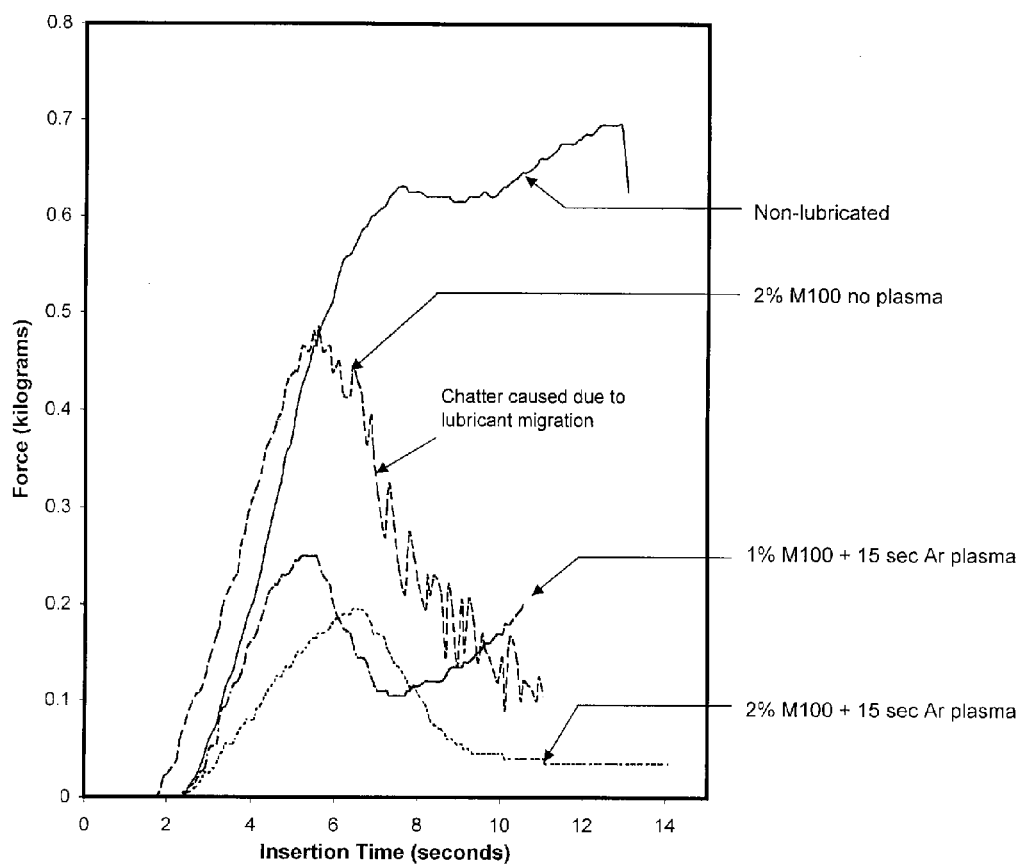
FIG. 8 is a plot of experimental measurements of the force applied to a syringe needle as a function of insertion time, where the needle was coated with various lubricants and treated for a specific time by an ionizing gas plasma at about atmospheric pressure. The force was measured as the needle was inserted into a pharmaceutical closure stopper.

Coating solutions were made by preparing a 99:1 and 98:2 mixture by weight of Fomblin Perfluorosolve™ PFS-1 and Fomblin M100® lubricant. The coating solutions were applied to clean 25-gauge syringe needles. The syringe needles were allowed to air dry to evaporate the solvent. After drying, the needles were exposed to an argon ionizing plasma at about atmospheric pressure for 15 seconds. The force required for penetration of the needles into pharmaceutical closure stoppers was measured using a digital force gauge. FIG. 8 illustrates the forces in kilograms for syringe needles prepared according to the following three scenarios: 1) no lubrication and no plasma treatment, 2) lubricated but no plasma treatment, and 3) lubricated and plasma treated. The penetration force was greatly reduced by the plasma treatment. The needle that was neither lubricated nor plasma treated required a force of about 0.7 kilograms. The lubricated but not plasma treated needle required a force of about 0.5 kilograms and exhibited chatter. The lubricated and plasma treated needles required a force of about 0.2 to 0.25 kilograms and exhibited no discernible chatter.

EXAMPLE 8

Figure 9:
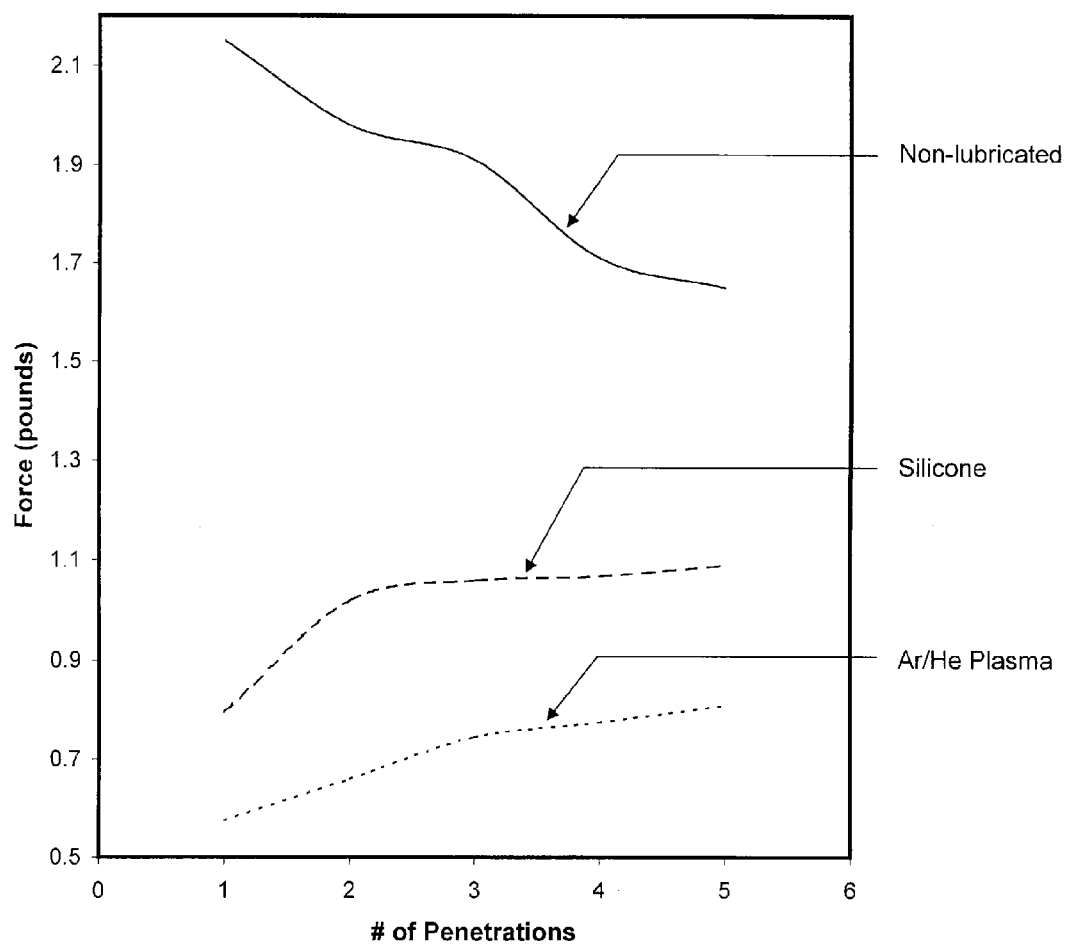
FIG. 9 is a plot of experimental measurements of the force applied to a syringe needle as a function of the number of penetrations into a pharmaceutical closure stopper, where the needle was coated with various lubricants and treated for a specific time by an ionizing gas plasma at about atmospheric pressure.

A coating mixture was made by preparing a 60:40 mixture by weight of Fomblin M100® and Fomblin ZDOL® lubricants. This mixture was then diluted 95:5 by weight with Fomblin Perfluorosolve™ PFS-1. The coating solution was applied to clean 21-gauge syringe needles. The syringe needles were then allowed to air dry to evaporate the solvent, leaving a thin layer of the lubricants on the surface. The syringe needles were then exposed to a helium ionizing plasma at about atmospheric pressure for 5 seconds. The syringe needles were then tested for penetration force into pharmaceutical closure stoppers for a total of 5 penetrations. FIG. 9 illustrates the peak forces in pounds for these samples in comparison to silicone-coated syringe needles that were not plasma treated and uncoated syringe needles. The penetration force was greatly reduced by the plasma treatment. The non-lubricated and not plasma treated needle required a force of about 2.1 pounds for the first penetration, falling to about 1.6 pounds after 5 penetrations. The needle coated with silicone but not plasma treated required a force of about 0.7 pounds for the first penetration, increasing to about 1.1 pounds after 5 penetrations. The needle that was lubricated and plasma treated required a force of about 0.6 pounds for the first penetration, increasing to about 0.8 pounds after 5 penetrations.

EXAMPLE 9

Figure 10:
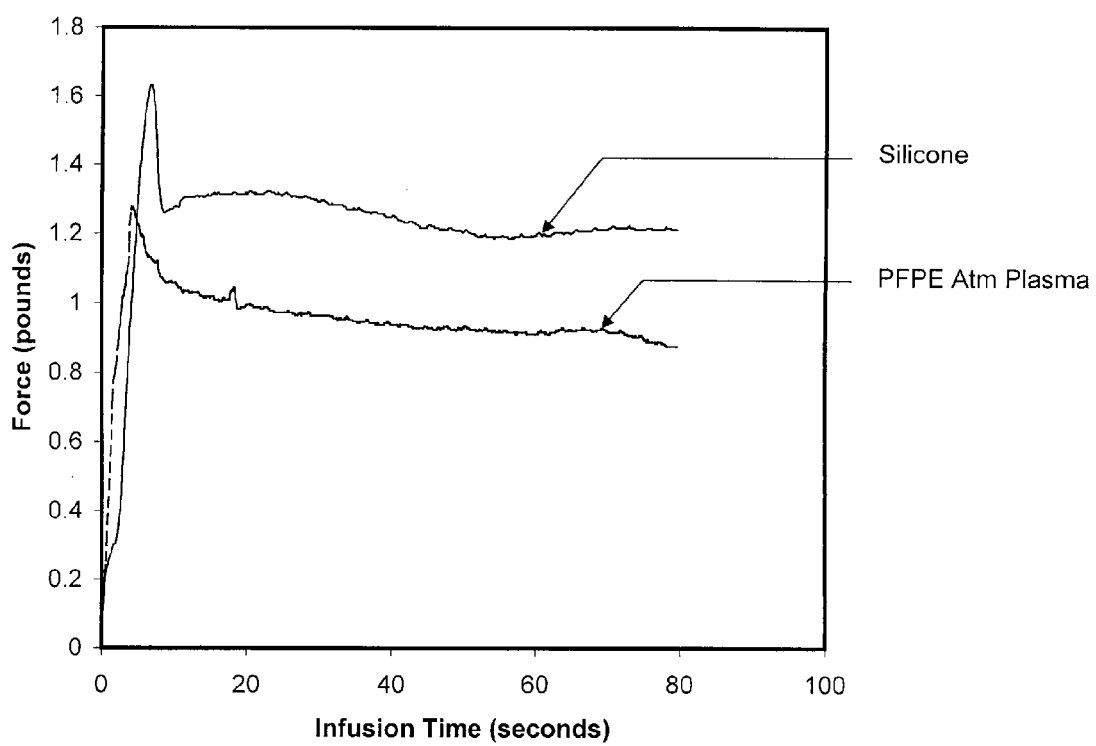
FIG. 10 is a plot of experimental measurements of the force applied to a syringe plunger as a function of infusion time, where the barrel of the syringe was made of glass and was coated with various lubricants and treated for a specific time by an ionizing gas plasma at about atmospheric pressure.

Glass syringes (size 10 cc), which are typically used in pre-filled syringes, were tested in this example. A coating solution was made by preparing a 25:25:50 mixture by weight of Fomblin ZDOL®, Fomblin M30®, and Fomblin M60®, respectively. The resulting coating solution contained 2% by weight of PFPE solids. After application of the coating solution to the inside of the syringe barrels, they were allowed to air dry to evaporate the solvent, leaving a thin layer of the lubricants on the surface. The syringe barrels were then exposed to a helium ionizing plasma at atmospheric pressure for 3 seconds. The syringes barrels were then assembled with butyl rubber plungers and 23 gauge cannula and parked for 3 days. The force required to infuse deionized water was then measured. FIG. 10 presents these data, as well as the force measurements for commercially available syringes pre-lubricated with silicone oil that were not plasma treated. The plasma treated syringes exhibit reduced force as compared to the syringes that were not plasma treated. The syringe that was lubricated with silicone oil but not plasma treated required a force of about 1.6 pounds to achieve break-out, then achieved a relatively constant sliding force of about 1.2 pounds. The lubricated and plasma treated syringe required about 1.3 pounds to achieve break-out, then achieved a relatively constant sliding force of about 1 pound. Neither syringe exhibited any discernible chatter,

EXAMPLE 10

Figure 11:
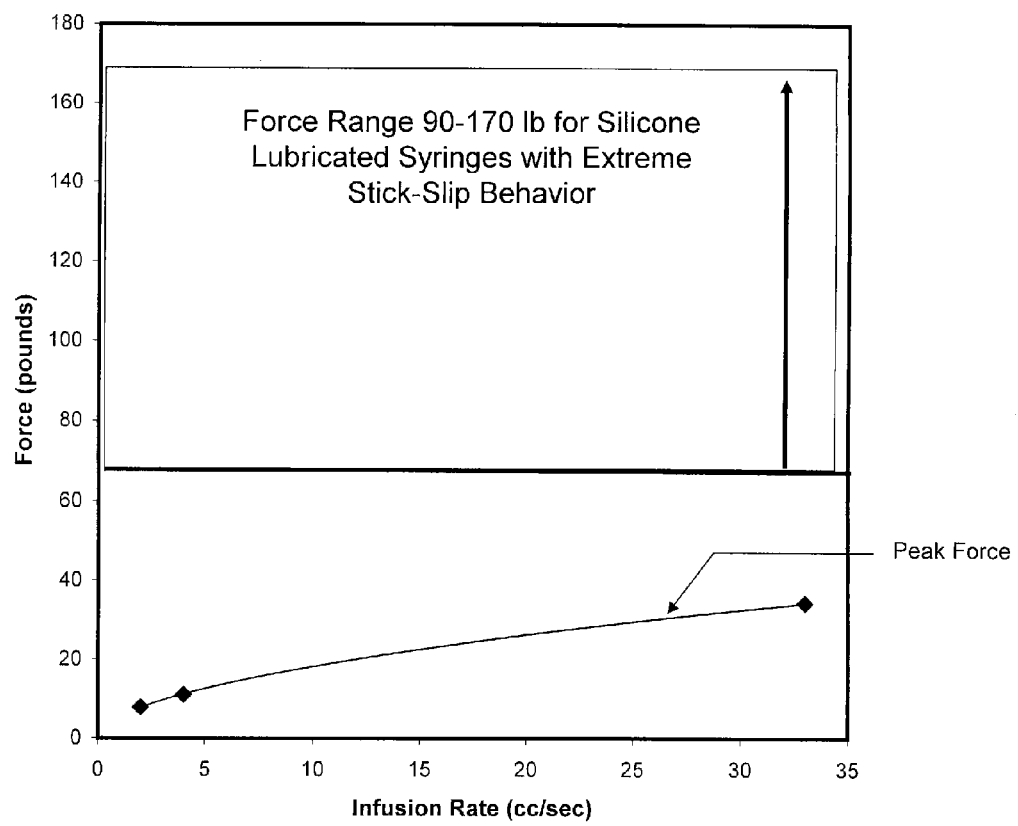
FIG. 11 is a plot of experimental measurements of the force applied to a syringe plunger as a function of infusion time, where the barrel of the syringe was coated with a specific lubricant and treated for a specific time by an ionizing gas plasma at about atmospheric pressure. The infusing medium was a high viscosity liquid.

Syringes (size 60 cc) used for power injection of contrast media were used in this example. The syringe barrels were made of PET polymer and the rubber plunger was butyl rubber. The contrast media used for infusion was Visipaque 320® manufactured by Amersham Health. Visipaque 320® is a viscous liquid with a viscosity of approximately 70 centipoise. Commercially available syringes pre-lubricated with silicone oil typically display forces in excess of 100 pounds when tested at typical infusion rates of 20-30 cc/sec. In this example, a coating solution was made by preparing a 90:10 mixture by weight of Fomblin Perfluorosolve™ PFS-1 and Fomblin M100® lubricant. The syringe barrels were filled with the coating solution and allowed to drain. The syringe barrels were allowed to air dry to evaporate the solvent, leaving a thin layer of the lubricant on the surface. After drying, the syringe barrels were exposed to a 50:50 argon and helium ionizing plasma at about atmospheric pressure for 20 seconds. The samples were then tested for infusion force of the contrast media. FIG. 11 shows the infusion forces at various infusion rates up to 35 cc/sec and clearly shows the lower forces observed in the syringe barrels that were lubricated and plasma treated as compared to the syringe barrels pre-lubricated with silicone oil, but not plasma treated. The syringe barrels that were not plasma treated required a force of about 90 to 170 pounds to achieve break-out depending on the infusion rate. The syringe barrels that were lubricated and plasma treated required only about 10 to 40 pounds to achieve break-out over the same infusion rate range.

EXAMPLE 11

Figure 12:
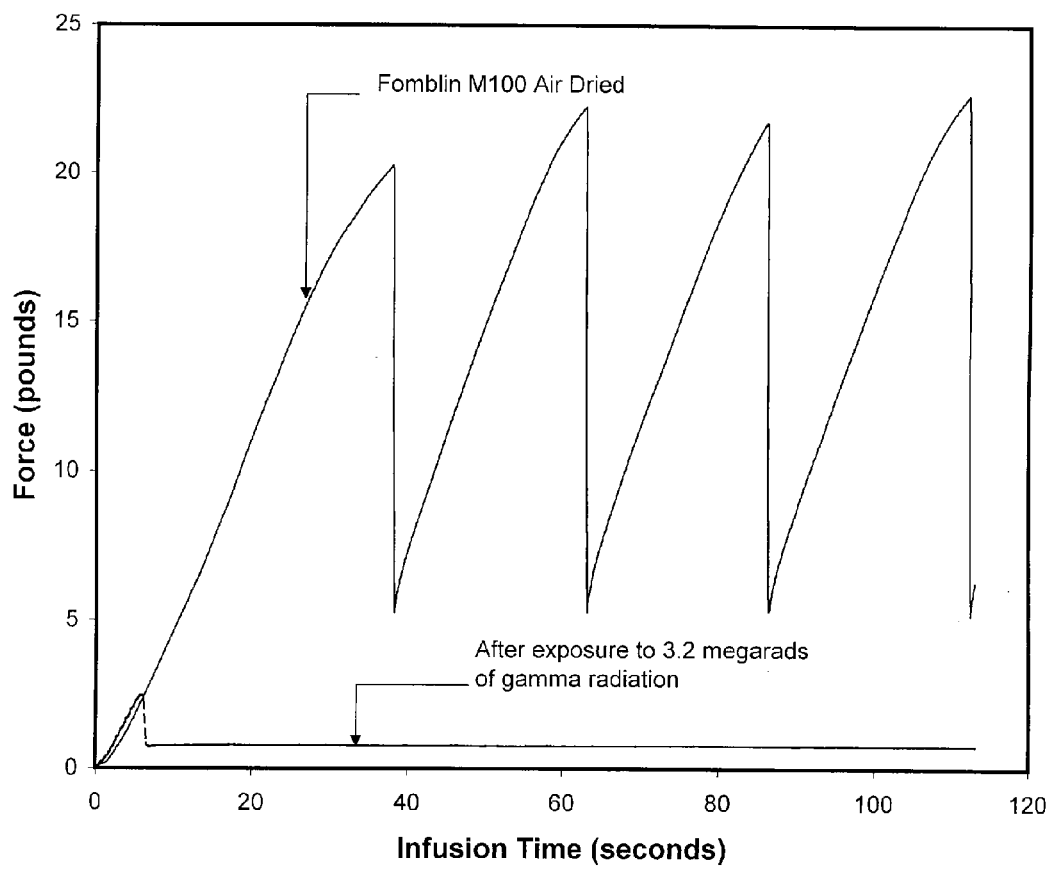
FIG. 12 is a plot of experimental measurements of the force applied to a syringe plunger as a function of infusion time, where the barrel of the syringe was coated with a specific lubricant and treated for a specific time by ionizing gamma radiation.
Figure 13:
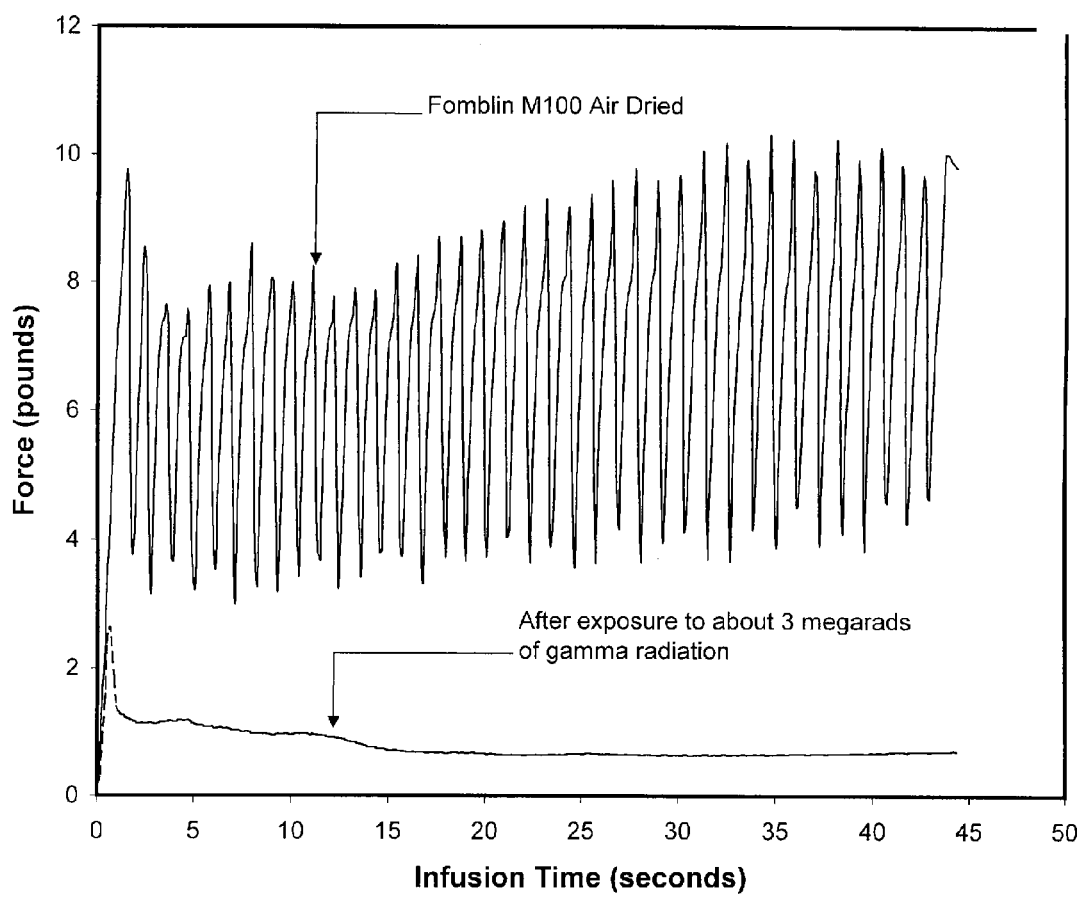
FIG. 13 is a plot of experimental measurements of the force applied to a syringe plunger as a function of infusion time, where the barrel of the syringe was coated with a specific lubricant and treated for a specific time by ionizing gamma radiation.

A coating solution was made by preparing a 90:10 mixture by weight of Fomblin Perfluorosolve™ PFS-1 and Fomblin M100® lubricant. Non-lubricated injection molded 10 cc polypropylene syringe barrels were filled with the coating solution and allowed to drain. The syringe barrels were allowed to air dry to evaporate the solvent, leaving a thin layer of the lubricant on the surface. The syringe barrels were then exposed to ionizing radiation that was generated using a cobalt-60 source. The total dose of exposure was about 3 megarads. The syringe barrels were tested for infusion forces before and after exposure to the ionizing radiation. FIG. 12 presents the resulting data for the syringe barrels exposed to the ionizing radiation and those not exposed to the ionizing radiation at an infusion rate of 1 cc/min, and FIG. 13 presents the resulting data for a similar test at an infusion rate of 10 cc/min. Both FIG. 12 and FIG. 13 demonstrate that the ionizing radiation energy source dramatically reduced break-out forces and eliminated stick-slip chatter. At an infusion rate of 1 cc/min, the syringe barrel that was lubricated but not exposed to the ionizing radiation required a force of about 20 to 22 pounds to achieve break-out and exhibited repeated chatter. The syringe barrel that was lubricated and exposed to the ionizing radiation required a force of about 2 pounds to achieve breakout and exhibited no discernible chatter. At an infusion rate of 10 cc/min, the syringe barrel that was lubricated but not exposed to the ionizing radiation required a force of about 7 to 10 pounds to achieve break-out and exhibited repeated chatter. The syringe barrel that was lubricated and exposed to the ionizing radiation required a force of about 3 pounds to achieve breakout and exhibited no discernible chatter.

EXAMPLE 12

Figure 14:
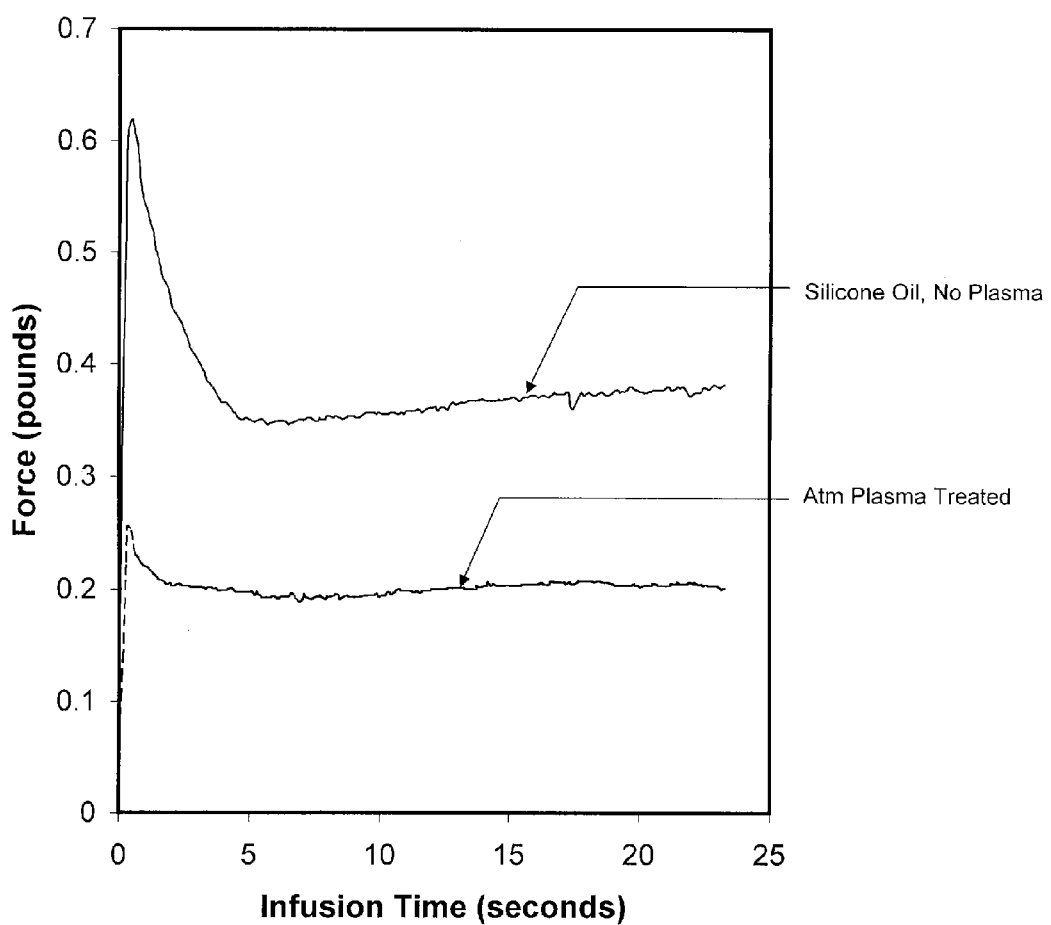
FIG. 14 is a plot of experimental measurements of the force applied to a syringe plunger as a function of infusion time, where the barrel of the syringe was treated for a specified time by ionizing gas plasma at about atmospheric pressure, coated with a specific lubricant, and treated for a specific time by an ionizing gas plasma at about atmospheric pressure.

Glass syringes (size 1 cc), which are typically used in pre-filled syringes, were tested in this example. A coating solution was made by preparing a 80:20 mixture by weight of Fomblin ZDOL® and Fomblin M03®, respectively. The resulting coating solution contained 5% by weight of the PFPE solids. The syringe barrel was first cleaned with deionized water and allowed to dry. The syringe barrels were then exposed to a 50:50 argon and helium ionizing gas plasma at about atmospheric pressure for 5 seconds. After exposure to the ionizing gas plasma, the coating solution was applied to the inside surface of the syringe barrel. The coated syringe barrel was then heated to accelerate the evaporation of the solvent, leaving a thin layer of the lubricant on the surface. The coated syringe barrels were then exposed to a helium ionizing gas plasma at about atmospheric pressure for 5 seconds. The syringes were then assembled with butyl rubber stoppers and 25 gauge needles. The force required to infuse deionized water at 1 cc/min was then measured for the treated syringe. FIG. 14 presents these data, as well as the force measurements for commercially available 1 cc glass syringes pre-lubricated with silicone oil but not plasma treated. The plasma treated syringe exhibited reduced force as compared to the syringe that was not plasma treated. The syringe that was lubricated with silicone oil but not plasma treated required a force of about 0.6 pounds to achieve break-out, then achieved a relatively constant sliding force of about 0.4 pounds. The plasma treated and lubricated syringe required a force of about 0.25 pounds to achieve break-out, then achieved a relatively constant sliding force of about 0.2 pounds. Neither syringe exhibited any discernible chatter.

We claim:

1. A method for preparing a lubricated surface of an article to reduce the break-out force and sliding frictional force, comprising:

(a) providing one or more surfaces;
(b) applying a lubricant to at least one of the surfaces to form a coated surface, the lubricant including a fluorochemical compound selected from the group consisting of a perfluoropolyether, a functionalized perfluoropolyether, a polychlorotrifluoroethylene and mixtures thereof; and
(c) exposing the coated surface to an ionizing gas plasma at about atmospheric pressure.

2. The method of claim 1 further comprising mixing the lubricant with a solvent to form a lubricant-solvent solution prior to applying the lubricant to the surface.

3. The method of claim 2 further comprising heating the coated surface, the heating step occurring after applying the lubricant-solvent solution to the surface and prior to exposing the coated surface to the energy source.

4. The method of claim 1 wherein applying the lubricant to at least one of the surfaces to form the coated surface comprises applying the lubricant to at least one of the surfaces to form the coated surface, wherein the lubricant contains additives selected from one or more groups comprising free radical initiators, viscosity modifiers, surfactants, wetting agents, anticorrosive agents, antioxidants, antiwear agents, buffering agents, dyes, and mixtures thereof.

5. The method of claim 1 wherein exposing the coated surface to the ionizing gas plasma further comprises forming the ionizing gas plasma from a gas selected from one or more groups comprising helium, neon, argon, krypton, air, oxygen, carbon dioxide, carbon monoxide, water vapor, nitrogen, hydrogen, and mixtures thereof.

6. The method of claim 1 further comprising additionally exposing the surface to the ionizing gas plasma prior to applying the lubricant.

7. The method of claim 1, wherein providing one or more surfaces comprises providing one or more surfaces constructed of polypropylene.

8. The method of claim 1, wherein providing one or more surfaces comprises providing one or more surfaces constructed of glass.

9. The method of claim 1, wherein providing one or more surfaces comprises providing a syringe barrel with an inner surface, the inner surface coated with a perfluoropolyether and exposed to the ionizing gas plasma at about atmospheric pressure after being coated with the perfluoropolyether.

10. The method of claim 9, wherein providing the syringe barrel with an inner surface comprises exposing the inner surface to the ionizing gas plasma prior to applying the perfluoropolyether.

11. The method of claim 10, wherein providing the syringe barrel comprises providing a polypropylene syringe barrel.

12. The method of claim 10, wherein providing the syringe barrel comprises providing a glass syringe barrel.

13. A method for preparing a lubricated surface of an article to reduce the break-out force and sliding frictional force, comprising
(a) providing one or more surfaces;
(b) exposing at least one of the surfaces to an ionizing gas plasma at about atmospheric pressure to form a plasma-treated surface; and
(c) applying a lubricant to the plasma-treated surface to form a coated surface, the lubricant including a fluorochemical compound selected from the group consisting of a perfluoropolyether, a functionalized perfluoropolyether, a polychlorotrifluoroethylene, and mixtures thereof.

14. The method of claim 13 further comprising mixing the lubricant with a solvent to form a lubricant-solvent solution prior to applying the lubricant to the plasma-treated surface.

15. The method of claim 14 further comprising heating the coated surface, the heating step occurring after applying the lubricant-solvent solution to the plasma-treated surface.

16. The method of claim 13 wherein applying the lubricant to the plasma-treated surface to form the coated surface comprises applying the lubricant to the plasma-treated surface to form the coated surface, wherein the lubricant contains additives selected from one or more groups comprising free radical initiators, viscosity modifiers, surfactants, wetting agents, anticorrosive agents, antioxidants, antiwear agents, buffering agents, dyes, and mixtures thereof.

17. The method of claim 13 wherein exposing at least one of the surfaces to the ionizing gas plasma at about atmospheric pressure comprises exposing at least one of the surfaces to the ionizing gas plasma at about atmospheric pressure, the ionizing gas plasma formed from a gas selected from one or more groups comprising helium, neon, argon, krypton, air, oxygen, carbon dioxide, carbon monoxide, water vapor, nitrogen, hydrogen, and mixtures thereof.

18. The method of claim 13, wherein providing one or more surfaces comprises providing an inner surface of a syringe barrel.

19. The method of claim 13, wherein applying the lubricant to the plasma-treated surface to form the coated surface comprises applying the lubricant to an inner surface of a syringe barrel to form the coated surface.

20. The method of claim 19, wherein applying the lubricant to the inner surface of the syringe barrel to form the coated surface comprises applying the lubricant to the inner surface of a glass syringe barrel to form the coated surface.

* * * * *